(12) United States Patent (10) Patent No.: US 8,301,254 B2
Mosesov et al. (45) Date of Patent: Oct. 30, 2012

(54) CROSS-BAND COMMUNICATIONS IN AN IMPLANTABLE DEVICE

(75) Inventors: Oleg F. Mosesov, Maple Grove, MN (US); Perry A. Mills, Arden Hills, MN (US)

(73) Assignee: Greatbatch Ltd., Clarence, NY (US)

( * ) Notice: Subject to any disclaimer, the term of this patent is extended or adjusted under 35 U.S.C. 154(b) by 1010 days.

(21) Appl. No.: 12/172,928

(22) Filed: Jul. 14, 2008

(65) Prior Publication Data

US 2008/0275312 A1 Nov. 6, 2008

Related U.S. Application Data

(63) Continuation-in-part of application No. 11/328,758, filed on Jan. 9, 2006, now abandoned.

(51) Int. Cl.
*A61N 1/00* (2006.01)
(52) U.S. Cl. ............... 607/30; 607/32; 607/60
(58) Field of Classification Search ............ 607/30, 607/32, 60
See application file for complete search history.

(56) References Cited

U.S. PATENT DOCUMENTS

| 5,487,760 | A | 1/1996 | Villafana |
| 5,562,713 | A | 10/1996 | Silvian |
| 5,961,019 | A | 10/1999 | Gleason et al. |
| 6,115,636 | A | 9/2000 | Ryan |
| 6,150,951 | A | 11/2000 | Olejniczak |
| 6,167,312 | A | 12/2000 | Goedeke |
| 6,169,925 | B1 | 1/2001 | Villaseca et al. |
| 6,240,317 | B1 | 5/2001 | Willaseca et al. |
| 6,379,300 | B1 | 4/2002 | Haubrich |
| 6,456,887 | B1 * | 9/2002 | Dudding et al. ............... 607/60 |
| 6,535,766 | B1 | 3/2003 | Thompson et al. |
| 6,740,075 | B2 * | 5/2004 | Lebel et al. ............... 604/891.1 |
| 6,763,269 | B2 * | 7/2004 | Cox ............... 607/60 |
| 6,993,393 | B2 | 1/2006 | Von Arx et al. |
| 7,047,076 | B1 | 5/2006 | Li et al. |
| 7,060,030 | B2 | 6/2006 | Von Arx et al. |
| 2002/0026224 | A1 | 2/2002 | Thompson et al. |
| 2002/0042637 | A1 | 4/2002 | Stover |
| 2002/0045920 | A1 | 4/2002 | Thompson |
| 2002/0065539 | A1 | 5/2002 | Von Arx et al. |
| 2002/0082665 | A1 * | 6/2002 | Haller et al. ............... 607/60 |
| 2002/0095195 | A1 | 7/2002 | Mass et al. |

(Continued)

OTHER PUBLICATIONS

International Search Report and Written Opinion, International Application No. PCT/US/2009/050505, mailed Sep. 28, 2009, 16 pages.

(Continued)

*Primary Examiner* — Nicole F Lavert
(74) *Attorney, Agent, or Firm* — Michael F. Scalise

(57) ABSTRACT

An ambulatory monitoring device includes a sensor to monitor a physiological signal and a battery power source. The device also includes a wireless receiver adapted to monitor a first frequency band having frequencies below 1 MHz and configured to detect and receive, using less than 10 microamps of current from the battery power source when operating, wireless communications within the first frequency band from a remote device at least one meter away. The device further includes a wireless transmitter adapted to transmit— after receipt from the remote device of a first wireless communication within the first frequency band that includes an invitation for further communication—a second wireless communication in a second frequency band having frequencies above 10 MHz, the second wireless communication comprising data indicative of the physiological signal as sensed by the sensor.

33 Claims, 3 Drawing Sheets

U.S. PATENT DOCUMENTS

| | | |
|---|---|---|
| 2002/0103514 A1 | 8/2002 | Abrahamson |
| 2002/0123776 A1 | 9/2002 | Von Arx et al. |
| 2002/0173702 A1 | 11/2002 | Lebel et al. |
| 2003/0114897 A1* | 6/2003 | Von Arx et al. ............ 607/60 |
| 2003/0114898 A1 | 6/2003 | Von Arx et al. |
| 2003/0149459 A1 | 8/2003 | Von Arx et al. |
| 2004/0049246 A1* | 3/2004 | Almendinger et al. ...... 607/60 |
| 2005/0070778 A1 | 3/2005 | Lackey et al. |
| 2006/0161222 A1 | 7/2006 | Haubrich et al. |
| 2006/0161223 A1 | 7/2006 | Vallapureddy et al. |
| 2007/0135855 A1 | 6/2007 | Foshee et al. |
| 2007/0153705 A1 | 7/2007 | Rosar et al. |
| 2007/0162089 A1 | 7/2007 | Mosesov |
| 2007/0167995 A1 | 7/2007 | Dudding et al. |
| 2007/0167996 A1 | 7/2007 | Dudding et al. |
| 2007/0185550 A1 | 8/2007 | Vallapureddy et al. |
| 2007/0239229 A1 | 10/2007 | Masoud et al. |
| 2007/0288066 A1 | 12/2007 | Christman et al. |

OTHER PUBLICATIONS

Memorandum Opinion and Order, In the matter of Biotronik, Inc. Equipment Authorization for Medical Implant Communications Service, FCC Identifier PG6BA0T, Adopted Feb. 12, 2003, Released Feb. 25, 2003, Before the Federal Communications Commission, Washington, DC 20554.

* cited by examiner

CROSS-BAND COMMUNICATIONS IN AN IMPLANTABLE DEVICE

CROSS-REFERENCE TO RELATED APPLICATION

This patent application is a continuation-in-part application. of the patent application having Ser. No. 11/328,758 and titled, "Cross-band Communications in an Implantable Device," filed Jan. 9, 2006, (U.S. Patent Application Pub. No. 2007/0162089), now abandoned, the entire contents of which are hereby incorporated by reference.

BACKGROUND OF THE INVENTION

The use of implantable medical devices has become increasingly commonplace as an effective method of monitoring the state and condition of a living body. An implantable medical device can be implanted within a human or an animal to monitor physiological parameters about the patient's well-being. By being implanted directly within the body, implantable medical devices can provide continuous monitoring of the patient's condition without requiring continuous onsite care by a caregiver or a physician. Implantable medical devices can also provide therapy within the body to change or improve the patient's physical state based on the physiological parameters received from sensors or the like. Implantable devices have been used to help treat a variety of physical disorders, such as heart disease, deafness, and diabetes with a large degree of success.

It is often desirable for such an implanted medical device to wirelessly communicate with a remote external device. For example, the implantable medical device may communicate the acquired physiological parameters to the external device for processing or display for other user output. The implantable medical device may also communicate to the remote device information about how the implantable medical device is configured, or the implantable medical device instructions for performing subsequent commands within the implantable medical device. Implantable medical devices typically use a predetermined frequency band to communicate information to and from the external device or programmer. One example of such a frequency band is the medical implant communication service (MICS) band, which operates between 402-405 MHz. The range of communication between the implantable medical device and the external device can be limited by a number of factors, including the limitations on the physical size of antennas that can be used within implantable device and signal loss due to transmission through the body of the patient.

The wireless communications to and from the implantable medical device are sent via the same frequency band, for example, the MICS frequency band. The MICS band can be split up into ten channels for transmission in the 402-405 MHz range. Regulations regarding the MICS band require the ten channels to be scanned through for the channel with the lowest ambient signal level to be transmitted on, or on the first available channel with an ambient signal below a given threshold. The scanning is typically performed by an external device and the selected channel is then communicated to the implantable medical device.

As wireless transmissions are sent between the implantable medical device and the external device, they can consume a significant amount of power during their operation. Implantable medical devices typically use an internal battery to power the device. The battery life or operational time that the implantable medical device can be used is an important factor in the design of the devices as a shortened battery life may require additional surgery to replace or recharge the device at an unwanted time for the patient. For this reason, it is desirable to reduce the power consumption within the implantable medical device to increase its time duration of operation.

Because of the power requirements needed to sustain an implantable medical device, some implantable medical devices use a sleep state where the device is kept in a low-current usage state. The implantable medical device periodically looks or "sniffs" for a wake-up signal from an external device. Upon receiving the wake-up signal, the implantable medical device is powered on to normal operation, which utilizes significantly more current than during the sleep state. Alternatively, a duty cycle mode can be used by an implantable medical device to achieve lower power consumption, where the device is turned on during operation for a short time period and turned off following operation. Power savings can be achieved by duty cycling, in that the implantable device is not continuously on.

BRIEF SUMMARY OF THE INVENTION

This disclosure is directed to ambulatory devices and their use in monitoring a patient's physiological parameters. More particularly, devices, systems, and methods for cross-band communications between an implantable medical device and an external device with increased power savings and an improved response time are described.

In a first general aspect, an ambulatory monitoring device includes a sensor to monitor a physiological signal of a subject and a battery power source. The ambulatory monitoring device also includes a wireless receiver adapted to monitor a first frequency band having frequencies below 1 MHz, where the wireless receiver is configured to detect and receive, using less than 10 micro-amps of current from the battery power source when operating, wireless communications within the first frequency band from a remote device when the monitoring device is at least 1 meter from the remote device. The ambulatory monitoring device further includes a wireless transmitter adapted to transmit—after receipt from the remote device of a first wireless communication within the first frequency band that includes an invitation for further communication—a second wireless communication in a second frequency band having frequencies above 10 MHz, the second wireless communication comprising data indicative of the physiological signal as sensed by the sensor.

In various implementations, the wireless receiver can be duty-cycled to monitor the first frequency band at some predetermined fraction of continuous time to conserve battery power. The receiver can monitor the first frequency band for 50 ms each second. In other implementations, the wireless receiver can continuously monitor the first frequency band. The first frequency band can be about 125 kHz to about 134 kHz, and the second frequency band can be about 402 MHz to about 405 MHz, or about 902 MHz to about 928 MHz. The first wireless communication within the first frequency band can include a selection of a channel within the second frequency band, and the wireless transmitter can transmit the second wireless communication at a frequency corresponding to the selected channel. Following the wireless transmitter's transmission of the second wireless communication within the second frequency band, the wireless receiver can receive from the remote device a third wireless communication within the first frequency band indicating that the remote device received the second wireless communication. The remote device can transmit the first wireless communication within the first frequency band periodically, such as at least once per day. In some implementations, the wireless receiver can use less than 3 micro-amps of current from the battery power source when operating. In some implementations, the wireless receiver uses less than 10 micro-amps of current from the battery power source when operating, and can receive wireless communications within the first frequency band from a remote device when the monitoring device is at least 2 meters from the remote device.

In another general aspect, a system for monitoring an ambulatory subject includes a remote device capable of wireless communication. The system also includes an implantable medical device for implantation in the ambulatory subject that includes: a sensor to monitor a physiological signal of the subject and a battery power source. The implantable medical device also includes a wireless receiver adapted to monitor a first frequency band having frequencies below 1 MHz, where the wireless receiver is configured to detect and receive, using less than 10 micro-amps of current from the battery power source when operating, wireless communications within the first frequency band from the remote device when the monitoring device is at least one meter from the remote device. The implantable medical device further includes a wireless transmitter adapted to transmit—after receipt from the remote device of a first wireless communication within the first frequency band that includes an invitation for further communication—a second wireless communication in a second frequency band having frequencies above 10 MHz, the second wireless communication comprising data indicative of the physiological signal as sensed by the sensor.

DETAILED DESCRIPTION OF THE INVENTION

Figure 1:
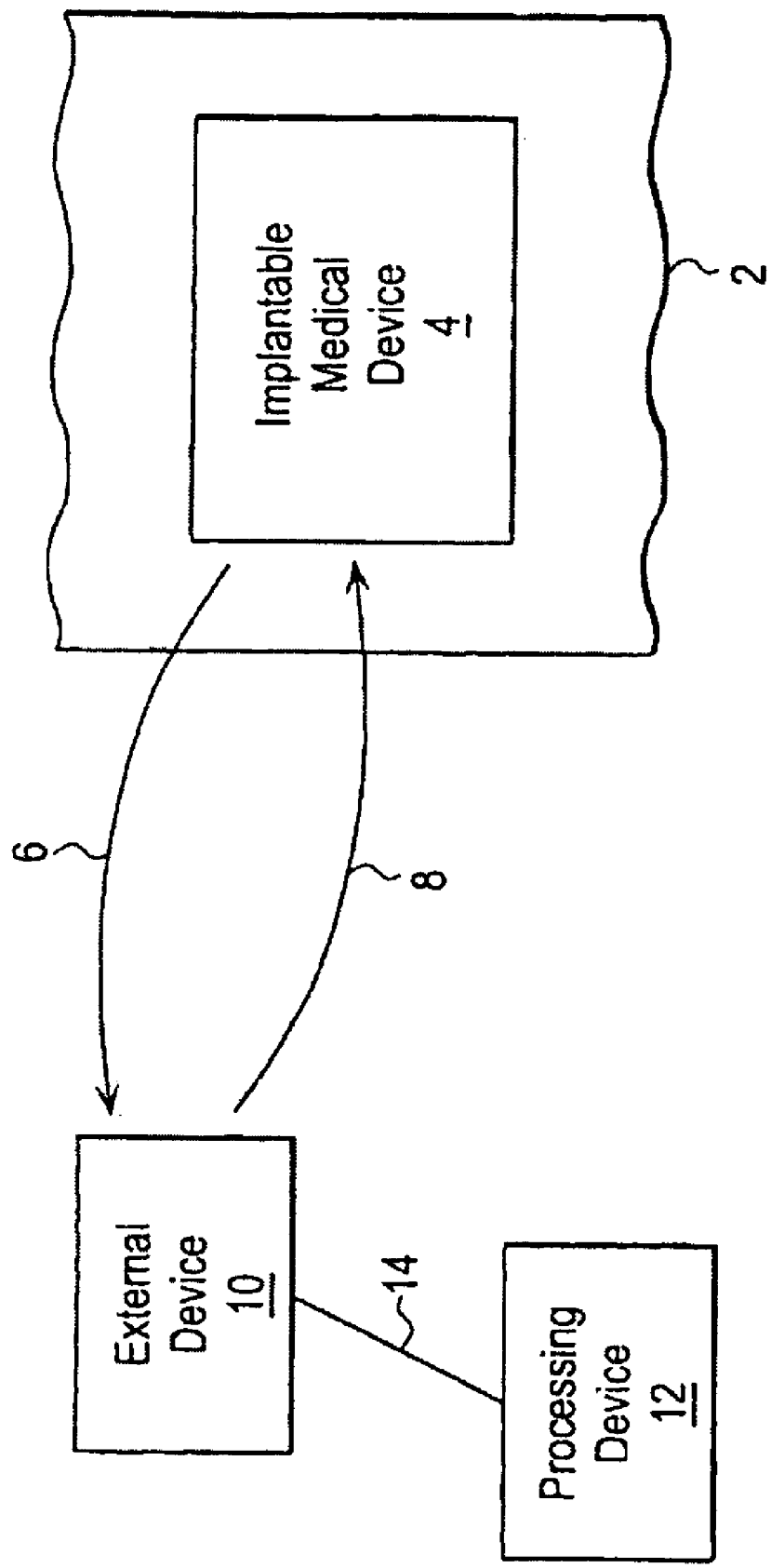
FIG. 1 is a simplified exemplary diagram showing wireless communications between an implantable medical device and an external device according to an implementation.

Described herein are implementations of an ambulatory monitoring device, such as a monitoring device that can be used to assess a condition of an ambulatory subject. The subject may be a human or an animal, and the ambulatory monitoring device may be implanted within the subject or external of the subject. The device may communicate wirelessly with a remote external device, and may do so using cross-band communications, or communications where inbound communications are received within a first frequency band, and outbound communications are transmitted within a second frequency band. In some cases, the first frequency band and the second frequency band may differ substantially, such as being separated by two, three, four, five, or more orders of magnitude. For example, the first frequency band may be a band in the hundreds of kilohertz range, while the second frequency band may be a band in the hundreds of megahertz range. By communicating with the external device in this fashion, the ambulatory device may conserve power because of a reduced current draw associated with monitoring a receive channel within the first (lower) frequency band as opposed to a larger current draw associated with a receiver that monitors the substantially higher second frequency band, for example.

In some implementations, the ambulatory monitoring device includes a sensor to monitor a physiological signal of a subject, and a battery power source. The device also includes a wireless receiver adapted to monitor a first frequency band having frequencies below 1 MHz, the wireless receiver configured to detect and receive, using less than ten micro-amps of current from the battery power source, wireless communications within the first frequency band from a remote device when the monitoring device is at least one meter from the remote device. That is, while the wireless receiver is operating to monitor a receive channel within the first frequency band, the receiver draws less than ten micro-amps of current from the battery, and in some implementations draws less than about five micro-amps or three micro-amps, while still being able to receive a communication from the remote device sent from a distance of one meter or more. In some implementations, current draw of ten micro-amps or less at distances of at least 2 meters are possible, and distances can go to three, four, or more meters also in some cases. Of course, communications over distances shorter than one meter are also possible in some implementations. The receiver can be configured such that there is low latency or delay in receiving transmissions from the external device. This low latency can be achieved by powering the receiver continuously or duty-cycling it at a rate fast enough to provide the desired low latency. The ambulatory monitoring device can further include a wireless transmitter adapted to transmit—after receipt from the remote device of a first wireless communication within the first frequency band indicating that the remote device is within an acceptable range for receipt of transmissions from the wireless transmitter in a second frequency band having frequencies above 10 MHz—a second wireless communication within the second frequency band and comprising data indicative of the physiological signal as sensed by the sensor.

FIG. 1 is a simplified exemplary diagram showing wireless communications between an implantable medical device and an external device according to an implementation. The body 2 of a subject (e.g., human patient or animal) has implanted therein an implantable medical device 4 to monitor physiological parameters and/or perform other functions within the body 2. The implantable medical device may be an electrocardiogram (ECG) device, a cardiac rhythm management device, a pacemaker, an endoscopic camera capsule, an implantable hearing device, or some other medical device that can be implanted within the patient's body 2. A surgical procedure may be used to insert the implantable medical device 4 within the patient's body 2. In alternative implementations, the device 4 is not an implantable device, but is rather a device external of the subject (e.g., worn externally or attached externally to the subject).

An external device 10 is provided to interact with the implantable medical device 4. Wireless communication 8 can be transmitted from the external device 10 in a first frequency band, and can be received by the implantable medical device 4. A wireless communication 6 can be transmitted from the implanted device 4 on a second frequency band for receipt by the external device 10. The external device 10 and the implanted device 4 may carry-on an interactive communications session in this fashion, with incoming messages (8) to the implantable device 4 within a first frequency band, and outgoing messages (6) from the implantable device 4 within a second, substantially different, frequency band.

The wireless communication 8 may be used to transmit a request for data measured by the implantable device sensors, acknowledge received data or other information transmitted by the implant, provide programming information to reconfigure the implantable medical device 4 or information modifying a therapy plan being performed by the implantable medical device 4, convey a selection of band or channel information for wireless communication 6 from the implantable medical device 4 to the external device 10, or the like. The wireless communication 6 from the implantable device 4 to the external device 10 may be used to transmit data that the device has measured or collected, or status information of the implantable device. In some cases, the information or data may be requested by the external device 10 (e.g., within the first communication). The communication 6 may also be used to acknowledge a request to start or end a communication session, for example.

A processing device 12 may be in communication (14) with the external device 10, and may process information received by the external device 10 from the implantable medical device 4, for example. The processing device 14 may be a computing device that can process the physiological data and/or other information received from the implantable medical device. The external device 10 and the processing device 12 may communicate over wired or wireless interface, and communication may occur over a network such as a local area network (LAN), wide area network (WAN), or the Internet. The processing device 12 may also be used for printing or displaying of the received information. In some implementations, the external device 10 and the processing device 12 are combined into a single device.

In an exemplary implementation, a patient is implanted with a medical device 4, and the medical device 4 periodically measures one or more physiologic signals within the patient over the course of the day. The device 4 may store the measured signal data in memory within the device 4, and may optionally process the data as is well known to a person having ordinary skill in the art. The external device 10 may comprise a base unit in the patient's home, for example, and may periodically attempt to initiate communications with the implantable medical device 4. For example, the external device may attempt to initiate communications at least once per day (or a few times per day, or hourly, etc.) with the implantable device 4. In one example, the external device 10 is near the patient's bed, and may attempt to initiate communications each night when it is likely that the patient is sleeping in the bed. The devices 10, 4 may then communicate as described herein. In another implementation, the external device 10 is a handheld device. For example, the device may be a dedicated device for interfacing with the implantable medical device or a general purpose device such as a personal digital assistant (PDA), mobile phone, or other type of device that the patient is likely to keep in proximity throughout the day.

Figure 2:
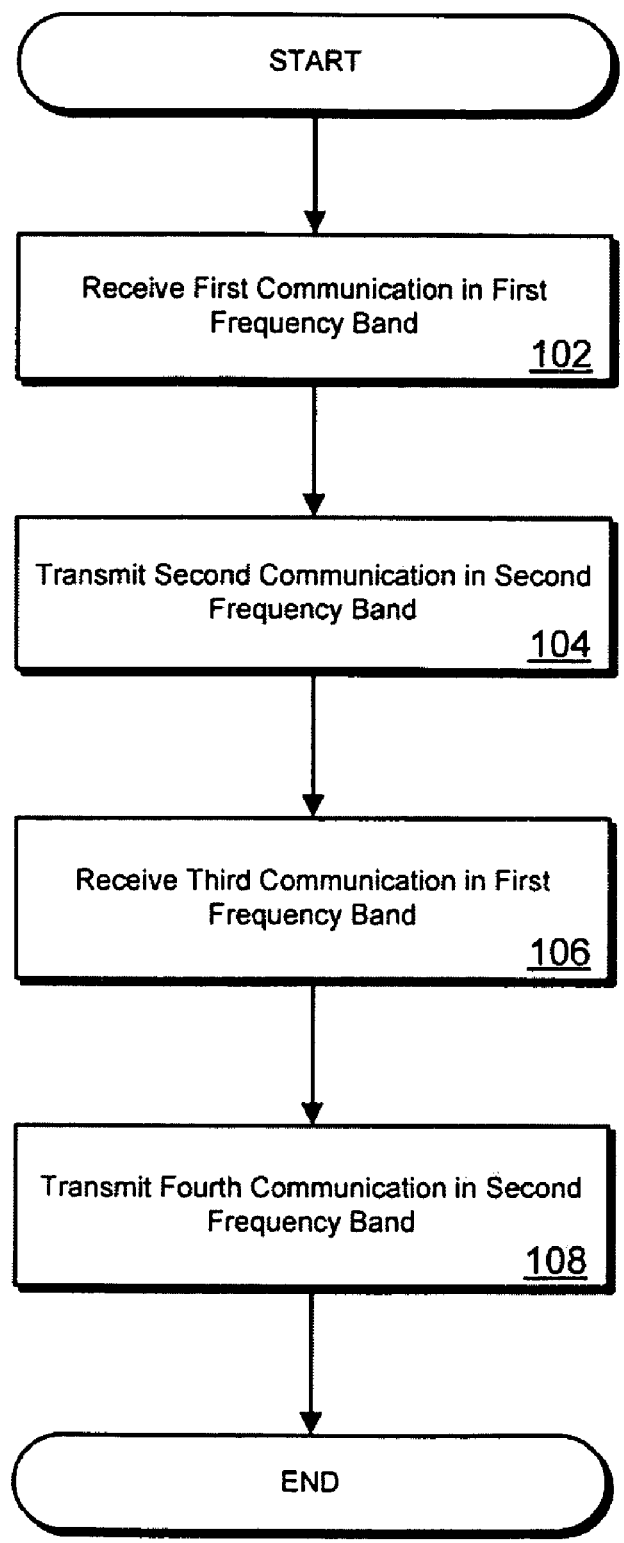
FIG. 2 is a flowchart of exemplary operations that can be performed to wirelessly communicate with an external device using cross-band communications.

FIG. 2 is a flowchart of exemplary operations that can be performed to wirelessly communicate with an external device using cross-band communications. The operations can be performed, for example, by an ambulatory device, such as a medical device implanted in an ambulatory subject. In step 102, a first communication in a first frequency band is received. The first communication may be received by a wireless receiver of the ambulatory device, and may have been sent by a wireless transmitter of a remote external device, for example. The first communication may be a request to start a communication session. In some cases, a timer within the external device may trigger transmission of the first communication, such as if the external device is programmed to periodically attempt communications with the ambulatory device. For example, the external device may be programmed to attempt communications with the ambulatory device once per day, once per hour, once every couple hours or few hours, etc. In other examples, a physician or patient may trigger the first communication via an external device user interface.

In some implementations, the first frequency band is lower than about 1 MHz. For example, the first frequency may be an RFID frequency in the range of about 125 kHz to about 134 kHz. Other low-frequency bands can also be used. The first frequency can be selected to be low enough that it can be received by an adequately sensitive receiver using adequately low power. The use of a receive channel frequency below 1 MHz in the implanted device may also minimize any reduction in telemetry range due to tissue attenuation. In some implementations, since the first frequency may be used to communicate limited amounts of command and control information to the implant, a sufficiently high data rate may still be achieved using the lower frequency.

At step 104, a second communication in a second frequency band is transmitted. The ambulatory device may transmit the second communication using a wireless transmitter, and may do so in response to receipt of the first communication from the external device. The second communication may be received by a receiver of the external device. In various implementations, the second communication may be used to indicate an acknowledgement of a received communication, to indicate that there is new data (e.g., measured physiologic data) available to be sent, or to communicate any appropriate message from the implantable device to the external device. The wireless communication may include, for example, physiological data monitored by the implantable medical device, status information about the implantable medical device, or an indication of an emergency medical event detected by the implantable medical device. The external device may receive the second communication, which in some cases may include physiologic signal information, and may process the communication, including processing the physiologic signal information in various implementations. In some cases, processing may occur in a device separate from the external device.

In some implementations, the second frequency band is higher than the first frequency band. In some implementations, the first frequency band may be substantially separated, frequency-wise, from the second frequency band. For example, the first frequency band may be a band of frequencies less than 1 MHz, while the second frequency band may be a band of frequencies above 10 MHz, 100 MHz, or 150 MHz. The second frequency band may be a MICS band in the range of 402-405 MHz, or a band in the range of about 902 MHz to about 928 MHz, or any other allowed frequency band. The second frequency band can be chosen to be high enough to achieve about 2 meters transmission range at a high data-rate with a relatively small antenna, and for low transmitted power. The information received by the implant receiver from the external device may comprise a selection of a frequency in a MICS band for the transmitter to send information to the external device.

At step 106, a third communication is received in the first frequency band. The third communication may be received by the wireless receiver of the ambulatory device, and may have been sent by the external device. In various implementations, the third communication may indicate an acknowledgement of prior data/information received by the external device, and/or a request for data. Battery power may be conserved in the implantable device because the device's receiver can receive communications at a lower frequency, even though the device's transmitter transmits at a much higher frequency. In this fashion, ongoing communications between the implantable device and the external device may occur, where communications from the external device to the implantable device are carried out in a lower frequency band, such as a band below about 1 MHz, and communications from the implantable device to the external device are carried out in a higher frequency band, such as a band above 10 MHz or above 100 MHz or 150 MHz. The ongoing communication pattern involving receipt at the implant of a communication on a lower frequency band and transmission from the implant on a higher frequency band may be repeated any number of times for a particular communications session. In some cases, the implantable device may transmit more than one communication in the second frequency band (e.g., two, three, four, or more) in response to receiving a communication in the first frequency band before another communication is received in the first frequency band. Similarly, in some cases the implantable device may receive a communication in the first frequency band and may not transmit a communication in response.

At step 108, a fourth communication in the second frequency band is transmitted. The ambulatory device may transmit the fourth communication in response to receipt of the third communication from the external device. The fourth communication may include a message that there is no additional data available to send.

In some implementations, communications received from the external device may include requests for specific information, such as data of a certain type or data stored in a particular location. In some implementations, communications sessions are always initiated by the external device, as by sending the first communication described above for receipt by the implantable device.

Several factors may be considered in determining timing and duration of the communications sessions and individual communications messages. For example, an amount of data for each communication may be selected such that data transfer is still efficient when coupled with overhead associated with each communication. An appropriate duration of each communication may depend on expected duration of any radio interference in some implementations. In some cases, spacing between communications may be extended to allow time for battery recovery in the implantable medical device or the external device.

Figure 3:
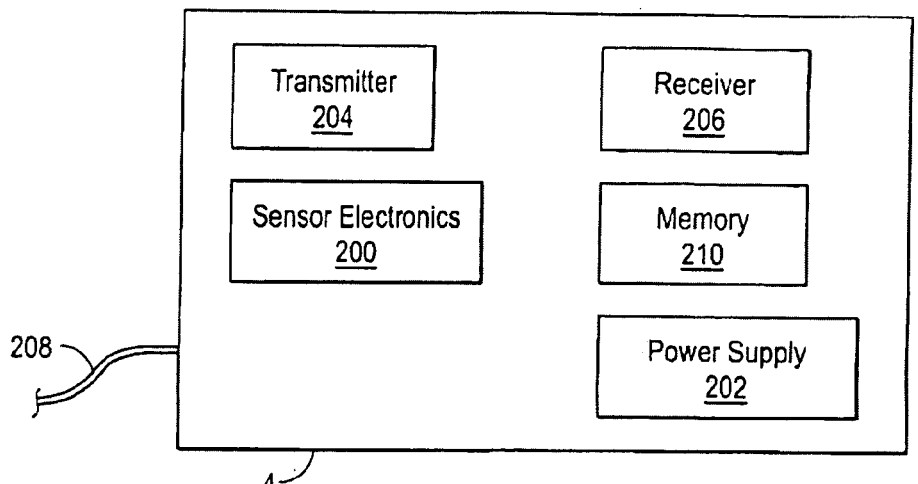
FIG. 3 is a simplified exemplary block diagram of an ambulatory medical device according to an implementation.

FIG. 3 is a simplified exemplary block diagram of an ambulatory medical device 4 according to an implementation. The device 4 need not be implantable, but will be referred to as such in the discussion that follows for simplicity. The implantable medical device 4 includes a number of different components contained within an external housing formed of a protective material designed to protect the components located within the external housing. For example, the protective material may be a lightweight plastic, titanium or epoxy material designed for implantation within the patient's body without any ill affects. A sensor 208 is provided for sensing any of a variety of the patient's physiological parameters, such as ECG or electrogram, blood pressure, body impedance, blood-oxygen saturation, pH, intracardiac temperature, and others. Of course, a plurality of sensors may be provided, such as an ECG sensor and a blood pressure sensor, or any other combination of the foregoing. The sensor 208 may be connected to the housing of the implantable medical device 4 or integrated directly within the housing of the implantable medical device 4. Sensor electronics 200 receive the information sensed by the sensor 208, and further process and convert the signal into a usable form that can be easily stored or further transmitted to an external device. Examples of signal processing provided by the sensor electronics 200 include digitizing the received parameters, providing time-contracted readback from one or multiple sensor signals, "chopping" multiple streams from the sensor together to form one output signal, and the like. A memory 210 may be provided for storage of the processed signals within the implantable medical device 4. The memory 210 may include a flash memory device or other solid-state memory storage device with a reduced form factor. The implantable medical device 4 further includes a power supply 202, a wireless transmitter 204, and a wireless receiver 206. The power supply 202 is typically a battery, but may be some other type of power supply. The battery or power supply voltage may be in a range of 1 to 3.6 volts. In some cases, the transmitter 204 and the receiver 206 may be formed as a transceiver.

The receiving and sending of wireless communications to and from the wireless device can represent a significant portion of the power consumption of the implantable medical device 4. For this reason, and to extend battery life of the implantable device, the receiver 206 can be an ultra-low power receiver that receives transmissions from the external device 10 at a lower frequency. The low frequency may be lower than about 1 MHz. For example, the frequency used may be an RFID frequency between about 125 kHz and 134 kHz. By using a lower frequency, the amount of current used in the implantable medical device 4 can be reduced and a reduced amount of power may be consumed during receiver operation as compared to devices that both send and receive on higher-frequency channels. For example, the amount of current being consumed by the ultra-low power receiver 206 may be about 2-3 µA, or less than 5 µA or 10 µA, depending upon the implementation, when operating to monitor and/or receive communications on a read channel. In any of the implementations described herein, the receiver 206 may be duty-cycled, such that it is not continuously operating to monitor for or receive communications on a communication channel. A receiving range of the receiver 206 may be about 2 meters and may be in a range of 1 meter to 4 meters, depending on the relative priority of long receiving range versus ultra-low power.

In some implementations, the receiver can be powered on continuously to achieve low latency when the implantable medical device is implanted into the body of the patient. In one embodiment, the implant receiver is powered and is receiving continuously so as to receive a signal from the external device immediately. In another embodiment, the power to the implant receiver may be duty-cycled to reduce power required from the battery. For example, the receiver may be on 50 milliseconds out of each 1 second interval, such that a signal sent from the external device will be received within one second, assuming the external device transmits continuously for at least one second. In other implementations, power-on duty-cycle periods of 10, 20, 30, 75, or 100 ms can be used, and intervals of two, three, or several seconds may be appropriate in some cases.

This low current draw by the implantable receiver 206 may be influenced by a variety of factors. For example, a low-frequency, high sensitivity antenna or coil may be utilized for the receiver, with a ferrite core having high permeability at the communication frequency, and with a high number of turns of wire. In some cases, size of the antenna or coil can be selected based on available space, such as to maximize the size given the available space. Circuitry may be used to amplify, filter, and decode signals received on the antenna, and may do so to achieve an acceptable gain-bandwidth at the low frequency using a minimal amount of current. The use of a low frequency receiver may allow use of low gain-bandwidth circuitry and a direct-conversion receiver that may not require additional power for a local oscillator or mixer, according to some implementations.

In one example, receiver 206 may receive transmissions as low as about 20-30 kHz, but in other examples the receiver 206 may receive transmissions on frequencies up to about 1 MHz. Due to the reduced amount of current being consumed, power management schemes such as sleep states or duty cycling may not be implemented in some implementations. Instead, implantable medical device 4, and in particular receiver 206, can be continuously left in an "ON" state during operation to continuously monitor for communications from an external device. This may improve latency or response time of the implantable medical device 4 because the device does may not need to be powered-on in response to a wake-up signal or duty cycled between on/off states. By removing the need for duty cycling or a sleep state, the circuitry of the implantable medical device can be simplified and reduced in size, according to some implementations. Of course, if some latency is tolerable, then the receive circuitry can be duty-cycled to use even less battery power.

Another advantage of the low-frequency receive channel is reduced signal attenuation due to body tissue. The signal propagation characteristics of the patient's body can tend to reduce the signal strength as the wireless communication from the external device passes through the patient's body before being received by implantable medical device. Lower frequency transmissions may tend to undergo a smaller loss in signal strength due to body attenuation than higher frequency transmissions.

The transmitter 204 can be used by the implantable medical device 4 to transmit wireless communications to an external device (e.g., device 10 of FIG. 1). For example, the transmitter 204 can be used to send wireless communications in an asymmetrical pattern with a second frequency band different from the first frequency band of the wireless communication received by the low-power receiver 206. That is, a pattern of communications back and forth between the implantable device 4 and the external device may involve receipt of communications in a first frequency band by the implantable device and transmit of communications in a second frequency band from the implantable device 4. A higher frequency band can be used to send the transmission from the transmitter 204, as the power consumption requirements for the receiver located in the external device 10 may not be as stringent as those of the implantable medical device 4. The external device 10 may be of a larger size than the implantable medical device 4, which may permit use of larger and more powerful batteries in the external device. Alternatively, an external power supply can be used to power the external device 10. The transmission frequency band from the implantable device 4 is typically higher than about 150 MHz. In one example, the frequency band being used by the transmitter 204 is the MICS band between 402 MHz and 405 MHz. In another example, the frequency band being used by the transmitter 204 is between about 902 and 928 MHz.

Figure 4:
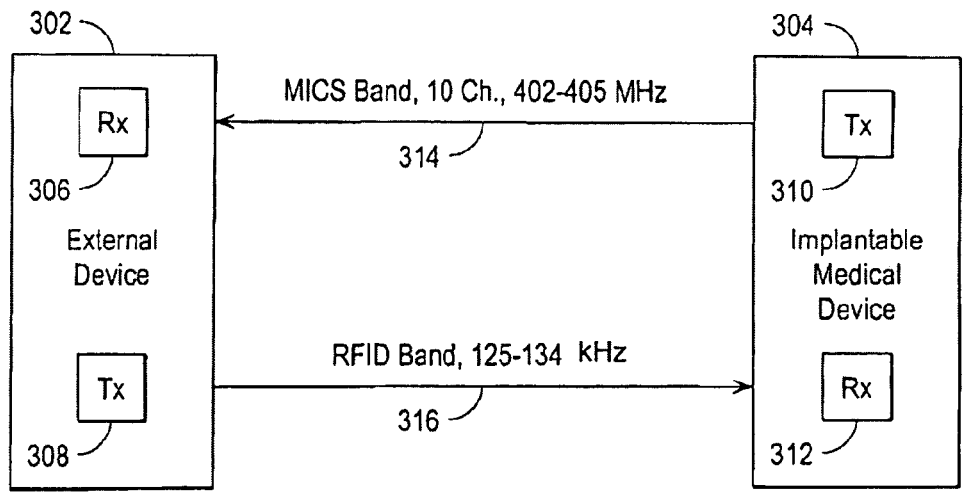
FIG. 4 is an exemplary diagram illustrating communications between an implantable medical device and an external device according to an implementation.

FIG. 4 is a simplified exemplary diagram illustrating communications between an implantable medical device 304 and an external device 302 according to a specific implementation. The external device 302 includes a receiver 306 and a transmitter 308. The implantable medical device 304 includes a transmitter 310 and a low-power receiver 312. A low frequency transmission 316 is sent from the transmitter 308 to the low-power receiver 312. The frequency band used for the transmission 316 is below about 1 MHz, and may be in the RFID frequency band between about 125 kHz and about 134 kHz. In some implementations, the information sent from the transmitter 308 may include a selection of a frequency in the MICS band for the implantable transmitter 310 to use in a transmission 314 from the transmitter 310 to the receiver 306 of the external device. The transmission 314 may be a transmission in the MICS band within one of ten channels between 402 and 405 MHz, for example, and may use the channel selected by the external device and communicated in communication 316, according to some implementations.

Figure 5:
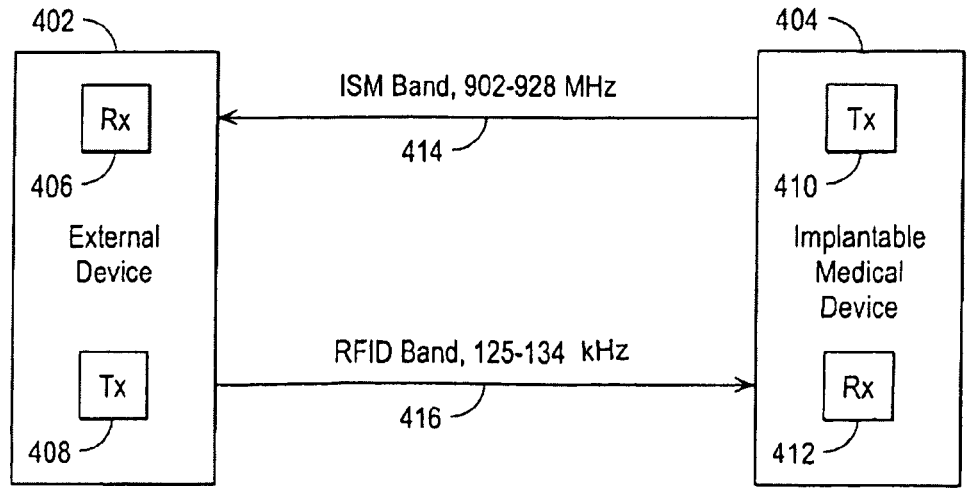
FIG. 5 is an exemplary diagram illustrating communications between an implantable medical device and an external device according to another implementation.

FIG. 5 is a simplified exemplary diagram illustrating communications between an implantable medical device 404 and an external device 402 according to another implementation. The external device 402 includes a receiver 406 and a transmitter 408. The implantable medical device 404 in this example is an ECG device that includes a transmitter 410 and a low-power receiver 412. A low frequency transmission 416 is sent from the transmitter 408 to the low-power receiver 412. The frequency band used for the transmission 316 is below about 1 MHz, and may be in the RFID frequency band between about 125 kHz and about 134 kHz. A transmission 414 from the transmitter 410 to the receiver 406 may be a transmission in the Industrial, Scientific and Medical (ISM) band between about 902 and about 928 MHz commonly used for ECG devices. In another example other frequency range may be utilized instead.

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims along with their full scope of equivalents.

What is claimed is:

1. An ambulatory monitoring device, comprising:
 a) a battery power source;
 b) a sensor powered by the battery and configured for monitoring a physiological signal of a subject;
 c) a wireless receiver that uses less than 10 micro-amps of current from the battery power source when operating and is configured to receive wireless communications from a remote device within a first frequency band of a range of frequencies below 1 MHz when the monitoring device is at least 1 meter from the remote device; and
 d) a wireless transmitter powered by the battery and that is separate from the receiver,
 e) wherein after receipt by the receiver of a first wireless communication from the remote device at the first frequency band, the wireless transmitter is configured to transmit a second wireless communication in a second frequency band of a range of frequencies above 10 MHz, and wherein the second wireless communication is of the physiological signal sensed by the sensor.

2. The ambulatory monitoring device of claim 1, wherein the wireless receiver is configured to duty-cycle as it monitors for the first frequency band at some predetermined fraction of continuous time to conserve battery power.

3. The ambulatory monitoring device of claim 1, wherein the receiver is configured to monitor the first frequency band for 50 ms each second.

4. The ambulatory monitoring device of claim 1, wherein the wireless receiver is configured to continuously monitor the first frequency band.

5. The ambulatory monitoring device of claim 1, wherein the first frequency band is from about 125 kHz to about 134 kHz.

6. The ambulatory monitoring device of claim 1, wherein the second frequency band is from about 402 MHz to about 405 MHz.

7. The ambulatory monitoring device of claim 1, wherein the second frequency band is from about 902 MHz to about 928 MHz.

8. The ambulatory monitoring device of claim 1, wherein the first wireless communication within the first frequency band includes a selection of a channel within the second frequency band, and wherein the wireless transmitter is configured to transmit the second wireless communication at a frequency corresponding to the channel.

9. The ambulatory monitoring device of claim 1, wherein following the wireless transmitter's transmission of the second wireless communication within the second frequency band, the wireless receiver is configured to receive a third wireless communication from a remote device, wherein receipt of the third wireless communication within the first frequency band indicates to the ambulatory monitoring device that the remote device received the second wireless communication.

10. The ambulatory monitoring device of claim 1, wherein the receiver is programmed to periodically receive the first wireless communication within the first frequency band.

11. The ambulatory monitoring device of claim 1 wherein the receiver is programmed to receive the first wireless communication within the first frequency band at least once per day.

12. The ambulatory monitoring device of claim 1 wherein the wireless receiver is configured to use less than 3 microamps of current from the battery power source when continuously operating.

13. The ambulatory monitoring device of claim 1, wherein the wireless receiver is configured to receive wireless communications within the first frequency band from a remote device when the monitoring device is at least 2 meters from the remote device.

14. The ambulatory monitoring device of claim 1 wherein the wireless transmitter draws a sufficient amount of current from the battery to transmit the second wireless communication in the second frequency band above 10 MHz to a receiver located in an external device.

15. A system for monitoring an ambulatory subject, the system comprising:
   a) a remote device capable of wireless communication; and
   b) an implantable medical device for implantation in the ambulatory subject, the implantable medical device comprising:
      i) a battery power source;
      ii) a sensor powered by the battery and configured for monitoring a physiological signal of the subject;
      iii) a wireless receiver that uses less than 10 micro-amps of current from the battery power source when operating and is configured to detect and receive wireless communications from the remote device within a first frequency band of a range of frequencies below 1 MHz when the monitoring device is at least one meter from the remote device; and
      iv) a wireless transmitter powered by the battery and that is separate from the receiver,
      v) wherein after receipt by the receiver of a first wireless communication from the remote device at the first frequency band, the wireless transmitter is configured to transmit a second wireless communication in a second frequency band of a range of frequencies above 10 MHz, and wherein the second wireless communication is of the physiological signal sensed by the sensor.

16. The system of claim 15, wherein the wireless receiver is configured to duty-cycle as it monitors the first frequency band at some predetermined fraction of continuous time.

17. The system of claim 15, wherein the wireless receiver is configured to continuously monitor the first frequency band.

18. The system of claim 15, wherein the remote device is configured to determine an appropriate channel within the second frequency band for communication with the implantable medical device.

19. The system of claim 18, wherein the first wireless communication within the first frequency band includes an indication of the appropriate channel within the second frequency band, and wherein the wireless transmitter is configured to transmit the second wireless communication at a frequency corresponding to the appropriate channel.

20. The system of claim 15, wherein following the wireless transmitter's transmission of the second wireless communication within the second frequency band, the wireless receiver is configured to receive a third wireless communication from the remote device, wherein receipt of the third wireless communication in the first frequency band indicates to the ambulatory monitoring device that the remote device received the second wireless communication.

21. The system of claim 15 wherein the wireless transmitter draws a sufficient amount of current from the battery to transmit the second wireless communication in the second frequency band above 10 MHz to a receiver located in an external device.

22. An ambulatory monitoring device, comprising:
   a) a battery power source;
   b) a sensor powered by the battery and configured for monitoring a physiological signal of a subject;
   c) a wireless receiver that uses less than 10 micro-amps of current from the battery power source when operating and is configured to detect and receive wireless communications from a remote device within a first frequency band of from about 125 kHz to about 134 kHz; and
   d) a wireless transmitter powered by the battery and that is separate from the receiver,
   e) wherein after receipt by the receiver of a first wireless communication from the remote device at the first frequency band, the wireless transmitter is configured to transmit a second wireless communication in a second frequency band having frequencies of from about 402 MHz to about 405 MHz, and wherein the second wireless communication is of the physiological signal sensed by the sensor.

23. The ambulatory monitoring device of claim 22 wherein the receiver is configured to receive the first wireless communication that includes an invitation for further communication.

24. The ambulatory monitoring device of claim 22 wherein the wireless transmitter draws a sufficient amount of current from the battery to transmit the second wireless communication in the second frequency band above 10 MHz to a receiver located in an external device.

25. An ambulatory monitoring device, comprising:
   a) a battery power source;
   b) a sensor powered by the battery and configured for monitoring a physiological signal of a subject;

c) a wireless receiver that is configured to detect and receive wireless communications from a remote device within a first frequency band of from about 125 kHz to about 134 kHz; and
d) a wireless transmitter that is separate from the receiver and uses less than 10 micro-amps of current from the battery power source when operating,
e) wherein after receipt by the receiver of a first wireless communication from the remote device at the first frequency band, the wireless transmitter is configured to transmit a second wireless communication in a second frequency band having frequencies of from about 902 MHz to about 928 MHz, and wherein the second wireless communication is of the physiological signal sensed by the sensor.

26. The ambulatory monitoring device of claim 25 wherein the receiver is configured to receive the first wireless communication that includes an invitation for further communication.

27. The ambulatory monitoring device of claim 25 wherein the wireless transmitter draws a sufficient amount of current from the battery to transmit the second wireless communication in the second frequency band above 10 MHz to a receiver located in an external device.

28. An ambulatory monitoring device, comprising:
a) a battery power source;
b) a sensor powered by the battery and configured for monitoring a physiological signal of a subject;
c) a wireless receiver that uses less than 10 micro-amps of current from the battery power source when operating and is configured to detect and receive wireless communications from a remote device within a first frequency band below 1 MHz; and
d) a wireless transmitter powered by the battery and that is separate from the receiver,
e) wherein after receipt by the receiver of a first wireless communication from the remote device at the first frequency band, the wireless transmitter is configured to transmit a second wireless communication in a second frequency band having frequencies above 10 MHz, and wherein the second wireless communication is of the physiological signal sensed by the sensor.

29. The ambulatory monitoring device of claim 28 wherein the wireless receiver is configured to communicate with a remote device when the ambulatory monitoring device is at least one meter from the remote device.

30. The ambulatory monitoring device of claim 28 wherein the wireless transmitter draws a sufficient amount of current from the battery to transmit the second wireless communication in the second frequency band above 10 MHz to a receiver located in an external device.

31. An ambulatory monitoring device, comprising:
a) a battery power source;
b) a sensor powered by the battery and configured for monitoring a physiological signal of a subject;
c) a wireless receiver that uses less than 10 micro-amps of current from the battery power source when operating and is configured to receive wireless communications from a remote device within a first frequency band of a range of frequencies below 1 MHz; and
d) a wireless transmitter powered by the battery and that is separate from the receiver,
e) wherein after receipt by the receiver of a first wireless communication from the remote device at the first frequency band, the wireless transmitter is configured to transmit a second wireless communication in a second frequency band of a range of frequencies above 10 MHz, and wherein the second wireless communication is of the physiological signal sensed by the sensor.

32. The ambulatory monitoring device of claim 31 wherein the wireless transmitter draws a sufficient amount of current from the battery to transmit the second wireless communication in the second frequency band above 10 MHz to a receiver located in an external device.

33. An ambulatory monitoring device, comprising:
a) a battery power source;
b) a sensor powered by the battery and configured for monitoring a physiological signal of a subject;
c) a wireless receiver that uses less than 10 micro-amps of current from the battery power source when operating and is configured to receive wireless communications from a remote device within a first frequency band of a range of frequencies below 1 MHz when the monitoring device is at least 1 meter from the remote device; and
d) a wireless transmitter that is separate from the wireless receiver,
e) wherein after receipt by the receiver of a first wireless communication from the remote device at the first frequency band, the wireless transmitter is configured to transmit a second wireless communication in a second frequency band of a range of frequencies above 10 MHz, and wherein the second wireless communication is of the physiological signal sensed by the sensor.

* * * * *